US007847817B2

(12) United States Patent
Negishi

(10) Patent No.: US 7,847,817 B2
(45) Date of Patent: Dec. 7, 2010

(54) ENDOSCOPE LIGHT SOURCE UNIT

(75) Inventor: Kiyoshi Negishi, Tokyo (JP)

(73) Assignee: Hoya Corporation, Tokyo (JP)

( * ) Notice: Subject to any disclaimer, the term of this patent is extended or adjusted under 35 U.S.C. 154(b) by 1189 days.

(21) Appl. No.: 11/428,673

(22) Filed: Jul. 5, 2006

(65) Prior Publication Data
US 2007/0010714 A1    Jan. 11, 2007

(30) Foreign Application Priority Data
Jul. 6, 2005    (JP)    ............... 2005-197300

(51) Int. Cl.
*A61B 1/06* (2006.01)
(52) U.S. Cl. ...................... 348/70; 600/180
(58) Field of Classification Search ............. 348/65, 348/68, 70, 72; 600/109, 180, 182, 178; 604/109
See application file for complete search history.

(56) References Cited

U.S. PATENT DOCUMENTS

| 4,803,550 | A | * | 2/1989 | Yabe et al. ............. 348/68 |
| 5,060,632 | A | * | 10/1991 | Hibino et al. ........... 600/109 |
| 6,322,497 | B1 | | 11/2001 | Takahashi |
| 2008/0294105 | A1 | * | 11/2008 | Gono et al. ............ 604/109 |

FOREIGN PATENT DOCUMENTS

| JP | 2003-305008 | 10/2003 |
| JP | 2006-006803 | 1/2006 |
| JP | 2006-006832 | 1/2006 |
| JP | 2006-051151 | 2/2006 |
| JP | 2006-136519 | 6/2006 |
| JP | 2006-149933 | 6/2006 |
| JP | 2006-149939 | 6/2006 |

OTHER PUBLICATIONS

U.S. Appl. No. 11/428,596 to Negishi, which was filed on Jul. 5, 2006.
U.S. Appl. No. 11/428,752 to Negishi, which was filed on Jul. 5, 2006.
English language Abstract of JP 2003-305008.
English language Abstract of JP 2006-6803.
English language Abstract of JP 2006-6832.
English language Abstract of JP 2006-051151.

* cited by examiner

*Primary Examiner*—Gims S Philippe
(74) *Attorney, Agent, or Firm*—Greenblum & Bernstein P.L.C.

(57) ABSTRACT

An endoscope light source unit includes an aperture device having aperture openings of different opening ratios, for selectively positioning one of the aperture openings between the incident end of a light guide and a light source; a driving device for moving the aperture device; an index detection device for detecting whether a specific aperture opening of the aperture device is positioned between the incident end face and the light source; an aperture opening position detection device for detecting whether any one of the aperture openings lies between the incident end face and the light source; a measuring device for measuring a driving amount of the driving device with respect to a position of the specific one of the aperture openings; and a controller for driving the driving device based on measurements from the index detection device, the aperture position detection device, and the measuring device.

7 Claims, 9 Drawing Sheets

ENDOSCOPE LIGHT SOURCE UNIT

BACKGROUND OF THE INVENTION

1. Field of the Invention

The present invention relates to an endoscope light source unit suitable for an endoscope, or an electronic endoscope, etc.

2. Description of the Related Art

Recent electronic endoscope systems have a processor with a built-in light source unit, to which an electronic scope having an electronic camera mounted on the distal end thereof or a fiber scope for conducting observation only through optical members is connected for use. In particular, electronic scopes have been provided for use with a wide variety of thicknesses and functions suited to different locations of observation. Processors connectable with various types of electronic scopes and fiber scopes must also have light source units that are compatible with such various electronic scopes and fiber scopes. For this reason, conventional light source units have been constructed so as to supply necessary amounts of light to electronic scopes that require maximum light intensities.

Such light source units are configured such that illumination light emitted from a high-intensity lamp is condensed by a condenser lens and made incident on the incident end face of a scope light guide, typically an optical fiber bundle. Since the necessary amount of illumination light varies with the type of electronic scope and with the observation location, the light source units are equipped with an aperture device for adjusting the amount of light mechanically. Among known aperture devices is one that includes a diaphragm which is composed of a partly-notched portion and an arm portion integrated with the partly-notched portion, having such a size that all the light from a light source lamp can be blocked; and a motor mechanically connected to an end of the arm portion. The motor is rotated to turn the diaphragm about the top of the arm portion, thereby adjusting the illumination intensity (see Japanese Patent Laid-Open Publication No. 2003-305008). Moreover, a light shielding plate may be provided with a plurality of aperture openings having different opening ratios or transmittances so as to form a rotary aperture plate which regulates the amount of light incident on the incident end face of a light guide by putting one of the aperture openings selectively between a light source unit and the incident end face of the scope light guide (i.e., into the illumination optical path). This rotary aperture plate is moved into the illumination light path at an aperture opening having an opening ratio (transmittance) corresponding to the scope.

As with the conventional aperture devices, the rotary aperture plate is driven with an open control and a relative rotation measurement which measures the driving amount for the rotary diaphragm plate to be driven from the initial position. The open-control driving, however, has a disadvantage that the rotary aperture plate can easily cause a shift in position due to vibration and impact. If the rotary aperture plate is continued to be used with a shift in position, aperture openings having opening ratios higher than an allowed opening ratio for the scope may be undesirably moved into the illumination optical path during use.

SUMMARY OF THE INVENTION

The present invention has been achieved in view of the foregoing problems of conventional endoscope light source units. The present invention provides an endoscope light source unit which can avoid a shift of the aperture for adjusting the amount of illumination light.

According to an aspect of the present invention, an endoscope light source unit is provided for making illumination light from a light source incident on an incident end face of a light guide connected thereto, the endoscope light source unit including an aperture device having a plurality of aperture openings of different opening ratios, for selectively positioning one of the aperture openings between the incident end face and the light source; a driving device for moving the aperture device; an index detection device for detecting whether a specific one of the aperture openings of the aperture device is positioned between the incident end face and the light source; an aperture opening position detection device for detecting whether any one of the aperture openings lies between the incident end face and the light source; a measuring device for measuring a driving amount of the driving device with respect to a position of the specific one of the aperture openings; and a controller for driving the driving device based on measurements from the index detection device, the aperture position detection device, and the measuring device.

It is desirable for the aperture device to include a rotary aperture disc. The rotary aperture disc includes the aperture openings, a index detection hole for detecting whether the rotary aperture disc is at an initial position of rotation, and a plurality of aperture position detection holes for detecting whether any one of the aperture openings lies between the incident end face and the light source, the aperture openings being formed at regular intervals circumferentially about the center of rotation of the rotary aperture disc. The index detection device includes an index sensor for detecting the index detection hole when the rotary aperture disc is at the initial position of rotation. The aperture opening position detection device includes an aperture position sensor for detecting whether any one of the aperture openings lies between the incident end face and the light source.

It is desirable for the driving device to include a stepping motor for driving the rotary aperture disc to rotate step by step in units of a predetermined angle; for the measuring device to measure a number of steps by which the stepping motor is driven from the initial position of rotation; and for the index detection hole is formed so as to be continually detected by the index sensor while the stepping motor is driven to rotate by a first predetermined number of steps in one direction, and further driven by a second predetermined number of steps in the same direction, and wherein one of the aperture position detection holes is detected by the aperture position sensor when driven by the second predetermined number of steps.

It is desirable for the controller to drive the stepping motor step by step until the index censor detects the index detection hole in the case where none of the aperture position detection holes are detected by the aperture position sensor after the first and second predetermined numbers of steps of driving.

It is desirable for the index detection hole and the aperture position detection holes to be formed at substantially same distances from the center of rotation of the rotary aperture disc; and for the index detection hole to be formed elongated in a circumferential direction of the rotary aperture disc so that the index detection hole continues to be detected by the index sensor while the stepping motor is rotated by a plurality of steps.

It is desirable for the index detection hole and the aperture position detection holes to be formed at different distances from the center of rotation of the rotary aperture disc so that the index detection hole is detected only by the index sensor and the aperture position detection holes is detected by the aperture position sensor.

It is desirable for the endoscope light source unit to include a display device for displaying an error indication when none of the aperture position detection holes is detected by the aperture position sensor after the first and second predetermined numbers of steps of driving.

According to the present invention, the endoscope light source unit can avoid a shift of the aperture for adjusting the amount of illumination light.

The present disclosure relates to subject matter contained in Japanese Patent Application No. 2005-197300 (filed on Jul. 6, 2005) which is expressly incorporated herein in its entirety.

DETAILED DESCRIPTION OF THE PREFERRED EMBODIMENT

Figure 1:
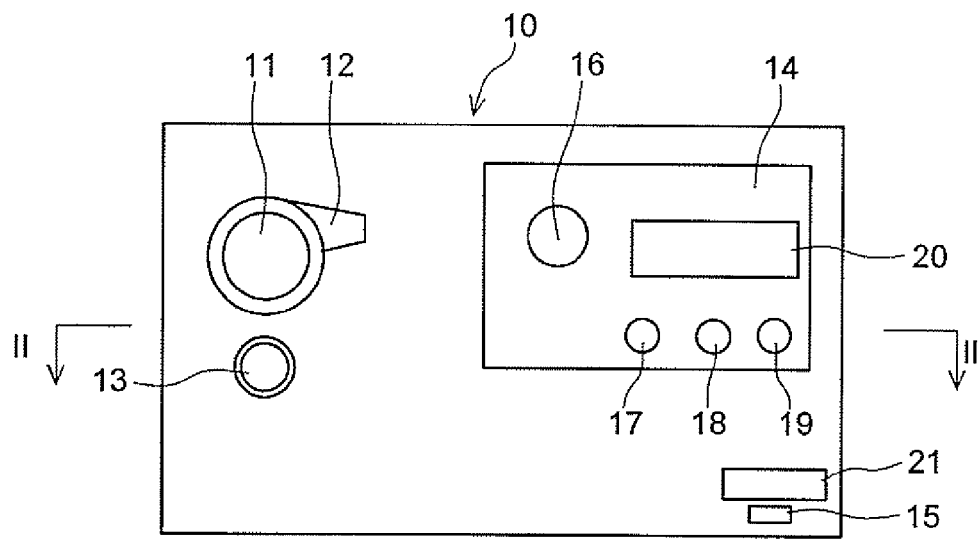
FIG. 1 is a front view showing an overview of an embodiment of a processor to which an endoscope light source unit according to the present invention is applied.
Figure 2:
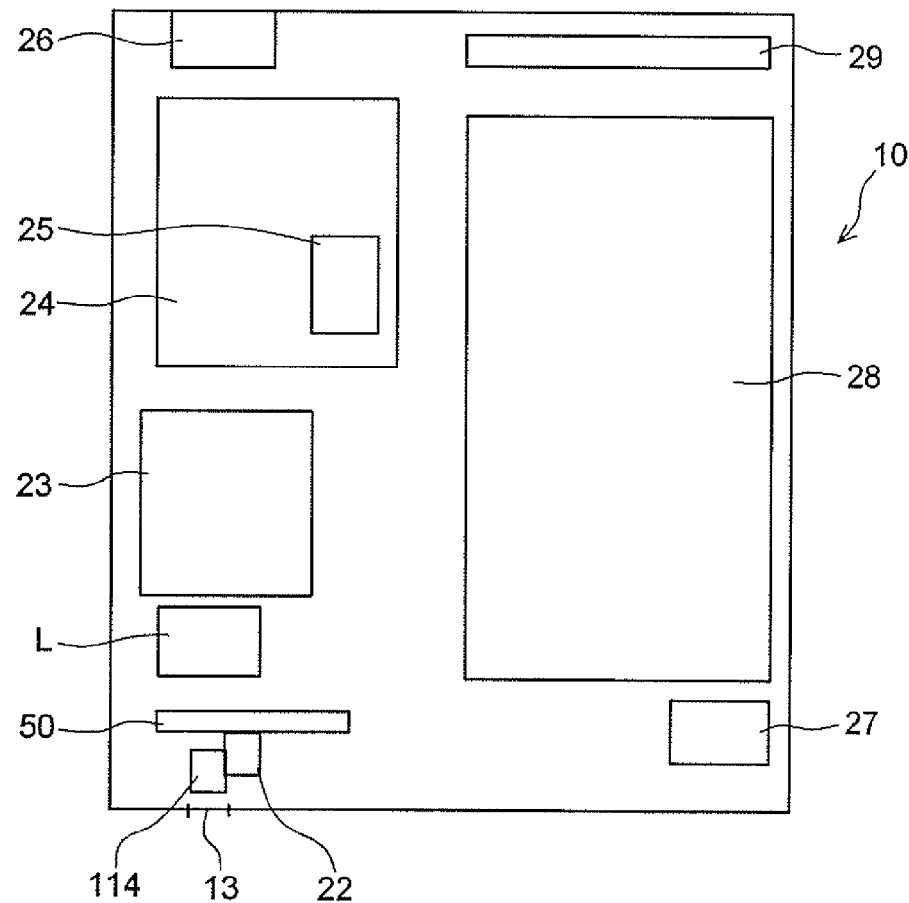
FIG. 2 is an abbreviated cross sectional view taken along the II-II line of FIG. 1, showing essential components of the processor.

Embodiments of the invention will be described with reference to the accompanying drawings. FIG. 1 is a front view of a processor (endoscope light source unit) 10 that contains a power supply unit to which the present invention is applied. FIG. 2 is an abbreviated cross sectional view taken along the II-II line of in FIG. 1, showing essential components of the processor 10.

The processor 10 is provided on the front thereof (as viewed in FIG. 1) with a scope socket 11 into which a connector 104 of an electronic scope 100 is to be inserted (see FIG. 4), and a scope lock lever 12 for locking the inserted connector 104 so as not to come off. The scope socket 11 establishes connection with connect pins, or the like, provided in the connector 104 of the electronic scope 100. A light guide socket 13 for the light guide connector 115 of the electronic scope 100 (or a fiber scope) to be inserted into is formed below the scope socket 11.

The processor 10 also has an operation panel 14 on the front, beside the scope socket 11. This operation panel 14 is provided with operation switches such as a lamp switch 16, an image quality adjustment switch (image quality adjustment button) 17, a light control selection switch (light control selection button) 18, a manual adjustment switch 19, and a scope information display 20. A memory card slot 21 for a removable memory card to be loaded into and a main switch 15 are also formed below the operation panel 14.

The processor 10 contains a rotary aperture plate 50 which is arranged behind the light guide socket 13. This rotary aperture plate 50 has a plurality of aperture openings having different opening ratios, which are arranged in the circumferential direction of this circular plate. An aperture plate drive motor (drive device) 22 rotationally drives so that any one of the aperture openings is opposed to an incident end face 113a of a light guide 113 which is plugged into the light guide socket 13 (see FIG. 4). A condenser lens L is arranged on the opposite side of the rotary aperture plate 50 from the incident end face 113a, with a lamp (light source) 23 provided behind the condenser lens L. As shown in FIG. 5, the light source 23 has a built-in high-intensity lamp 35. Illumination light emitted from the lamp 35 is focused by the condenser lens L so that the light beam passing through any one of the aperture openings of the rotary aperture plate 50 is incident on the incident end face 113a. The vicinity of the incident end face 113a of the light guide 113 is fixed inside a light guide sleeve 114 which is made of metal.

As shown in FIG. 2, the processor 10 also contains a lamp power supply 24 which has an igniter 25 for turning on the light source 23. A cooling fan 26 for cooling the lamp power supply 24 is formed on the rear panel of the processor 10.

In the processor 10, a memory card board 27 is arranged near the memory card slot 21. The memory card board 27 is electrically connected with the memory card loaded in the memory card slot 21, and functions as an interface circuit controls reading and writing from/to the memory card. For example, the read/write control includes reading information written in the memory card, and writing information such as image information processed by the processor 10 to the memory card. The processor 10 also contains a control board 28 on which circuits such as a control circuit (controller/index detection device/aperture opening position detection device) 41 and an image processing circuit are mounted. The control circuit 41 controls the operations of the entire processor 10, including the control of the memory card board 27 and the aperture plate drive motor 22. The image processing circuit of the control board 28 reads stored information from an EEPROM (memory) 109 of the electronic scope 100, drives a CCD sensor (image pickup device) 105 of the electronic scope 100, processes picture signals obtained by the CCD sensor 105, and displays the processed picture signals on a monitor display 43. The picture signals processed by the control board 28 are output from a picture connector (not shown) provided on a back panel substrate 29. A predetermined picture is then displayed on the monitor display 43.

Figure 3:
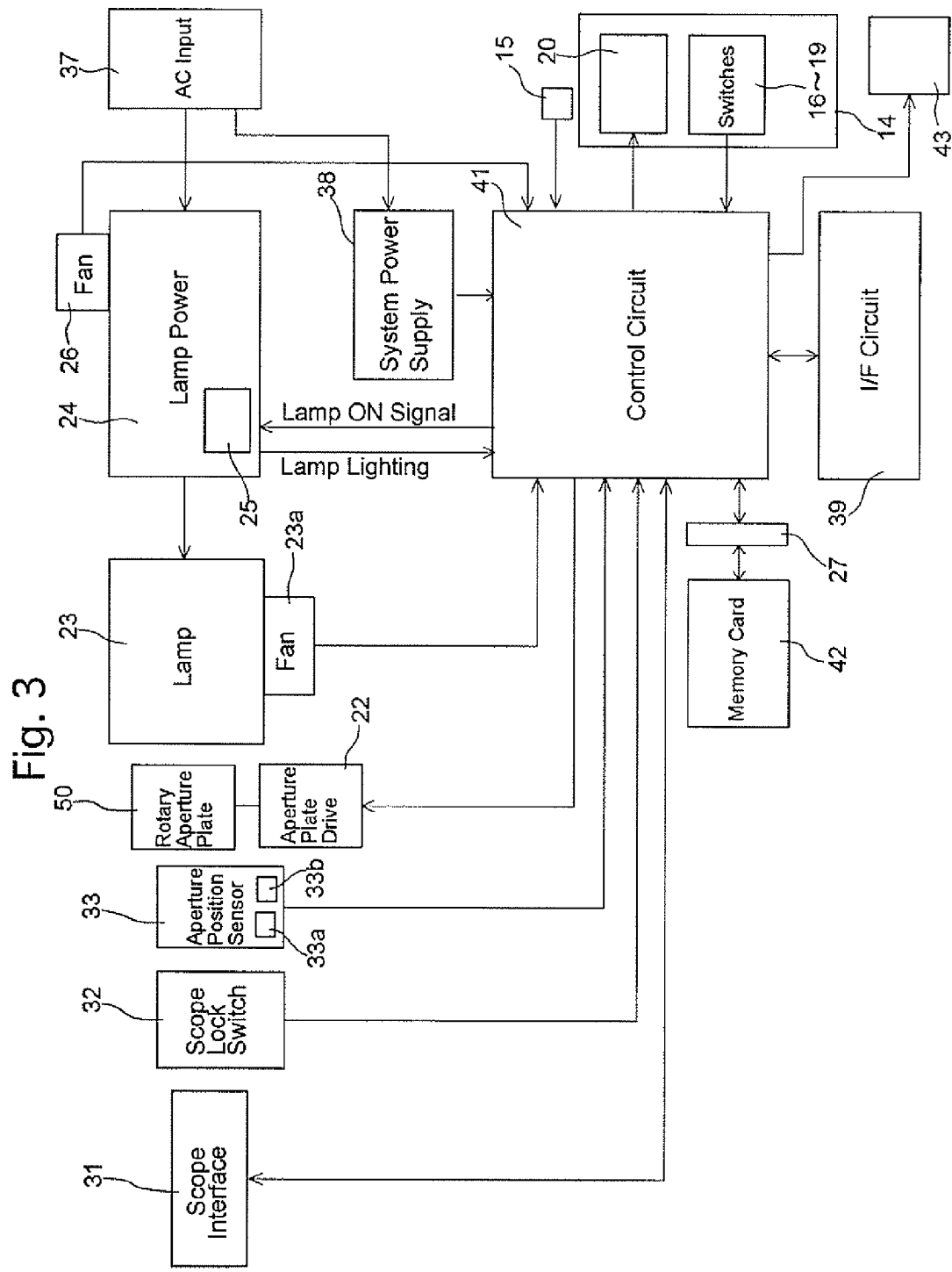
FIG. 3 is a block diagram showing essential circuits of the processor, according to the present invention.

FIG. 3 shows essential components of the circuit configuration of the processor 10. A scope interface 31 is provided inside the scope socket 11. The scope interface 31 is provided with a plurality of connectors, including an information connector and the picture connector. The information connector is for reading information written in the EEPROM 109 of the electronic scope 100. The picture connector transmits a drive clock of the CCD sensor 105, and inputs picture signals output from the CCD sensor 105. Each connector is connected to respective corresponding terminals, such as those of the control circuit 41 formed on the control substrate 28.

A scope lock switch 32 is a detection switch for detecting if the scope lock lever 12 is in a locked state. The state signal of the scope lock switch 32 is input to the control circuit 41.

The aperture plate drive motor 22 for driving the rotary aperture plate 50 rotationally is driven and controlled by the control circuit 41. Whether or not any one of the aperture openings of the rotary aperture plate 50 lies in the illumination light path is detected by an aperture position sensor 33 (33a and 33b), and the detection signal is input to the control circuit 41.

The light source 23 is turned on by the igniter 25 of the lamp power supply 24 which is controlled ON/OFF by the control circuit 41. The light source 23 is also provided with a lamp cooling fan 23a. The lamp cooling fan 23a is driven and controlled by the control circuit 41. The igniter 25 for turning ON and driving the light source 23 is driven by the lamp power supply 24 which is powered by an AC input 37, typically a commercial alternating-current power.

The AC input 37 also powers a system power supply 38 which outputs a constant voltage for driving electronic circuits such as the control circuit 41. The control circuit 41 is activated to start processing when the main switch 15 is turned ON, and transmits a lamp-ON signal to the lamp power supply 24 to turn ON the light source 23 via the igniter 25 when the lamp switch 16 is turned ON.

The control circuit 41 reads aperture-related information from the EEPROM 109 of the electronic scope 100 via the scope interface 31, and selects a maximum opening ratio of the rotary aperture plate 50 for use when adjusting the amount of the illumination light. In this case, the scope interface 31 functions as reading device.

The control circuit 41 also performs image capturing processing for driving the CCD sensor 105 of the electronic scope 100 and inputs an image signal from the CCD sensor 105 via the scope interface 31. Moreover, the control circuit 41 performs a predetermined image signal process, and displays the image signal on the monitor display 43 or writes the image data thereof to the memory card 42 via the card board 27. It should be appreciated that if the control circuit 41 starts the image capturing process when the main switch 15 is turned ON, the image capturing process is usually performed by the image processing circuit which is separate from the control circuit 41.

The control circuit 41 is also connected with an input device such as a keyboard via an I/F circuit 39 so that individual information necessary for endoscopic inspection can be entered via the input device.

Figure 4:
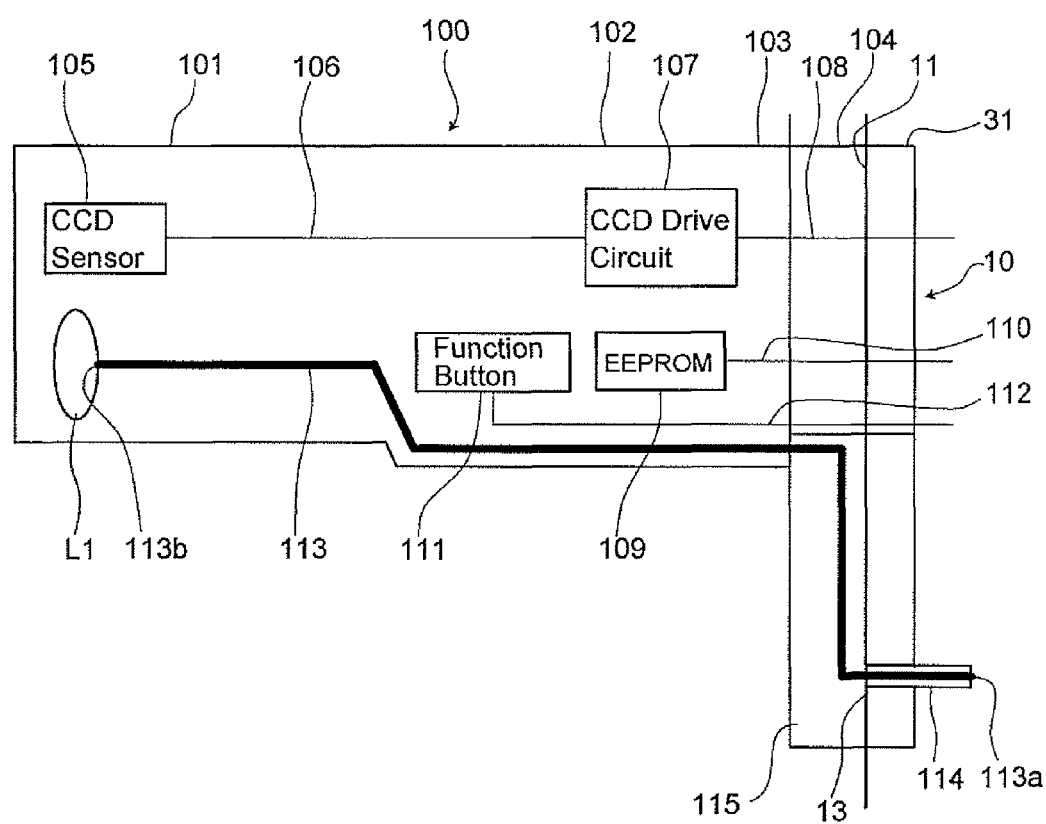
FIG. 4 is a schematic diagram of an electronic scope which is connectable to the processor, according to the present invention.
Figure 5:
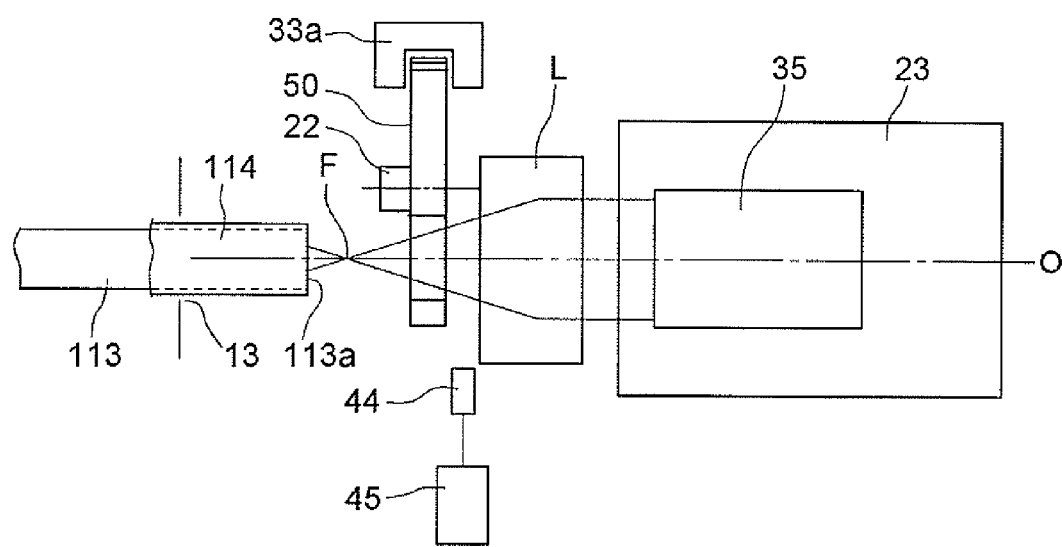
FIG. 5 is an explanatory diagram showing various components which are provided near the light source unit of the processor.

FIG. 4 is a diagram showing a schematic view of the electronic scope 10 which is connected to the processor 10. As shown in FIG. 4, the electronic scope 100 has a flexible insertion portion 101 and an operation portion 102. The connector 104 is arranged on the top of a universal tube 103 which extends from the operation portion 102. The CCD sensor 105 and a light distribution lens L1 for light illumination are arranged at the distal end of the flexible insertion portion 101. The CCD sensor 105 is connected to a CCD drive circuit 107 formed in the operation portion 102, via a picture line 106 which is laid through the insertion portion 101. The CCD drive circuit 107 is also connected with a picture transmission line that is laid through the operation portion 102 and the universal tube 103. The picture transmission line 108 is connected to signal pins formed in the connector 104. The EEPROM 109, containing such information as the type of the electronic scope 100, is provided in the operation portion 102.

A read/write line 110, which is connected with input and output terminals of the EEPROM 109, is connected to signal pins of the connector 104. The operation portion 102 also includes a function button 111 for making operations of taking a moving image, and photographing a still image, etc. A switch line 112 in connection with the contacts of the function button 111 is connected to signal pins in the connector 104. The picture line 108 is connected to the control circuit 41 via the signal pins when the connector 104 is connected to the scope interface 31. Furthermore, the picture signals of an image picked up by the CCD sensor 105 and output therefrom are input to the control circuit 41.

An EEPROM 109, containing information such as the type of scope, i.e., the electronic scope 100, is implemented in the operation portion 102. A read/write line 110 in connection with input and output terminals of the EEPROM 109 is connected to signal pins in the connector 104. The operation portion 102 also includes a function button 111 for making operations such as taking a moving image, and photographing a still image, etc. A switch line 112 in connection with the contacts of the function button 111 is connected to signal pins in the connector 104.

The exit end 113b of the light guide 113 is placed behind the light distribution lens L1. The light guide 113 is introduced through the insertion portion 101, the operation portion 102, the universal tube 103, and the connector 104, and is inserted and fixed inside the light guide sleeve 114 which protrudes out of the connector 104. The incident end face 113a of the light guide 113 is opposed to the open end of the light guide sleeve 114.

The EEPROM 109 provided in the electronic scope 100 contains at least the information for identifying the type of the scope. In this embodiment, scope types are classified into a plurality of groups stepwise depending on the maximum amounts of illumination light, i.e., the maximum amounts of light allowed for the light guide 113 to emit.

FIG. 5 is a diagram showing various components which are provided near the light source 23 of the processor 10. As shown in FIG. 5, the rotary aperture plate 50 is interposed between the incident end face 113a of the light guide sleeve 114 (light guide 113), which is inserted in the light guide socket 13, and the condenser lens L which is provided in front of the light source 23. The incident end face 113a is normally placed orthogonal to the illumination optical axis O of the condenser lens L, away from the focal point F of the condenser lens L. The substantially parallel illumination light emitted from the lamp 35 is focused at the focal point F by the condenser lens L, so that the light beam passing through the rotary aperture plate 50 gathers at the focal point F and thereafter diverges so as to be incident on the incident end face 113a. The illumination light beam entering from the incident end face 113a is guided through the light guide 113, and emitted from the exit end face 113b (see FIG. 4) of the light guide 113 provided at the distal end of the insertion portion 101. The emitted light then passes through the light distribution lens L1 for distribution (FIG. 4) so as to illuminate an object.

Figure 6:
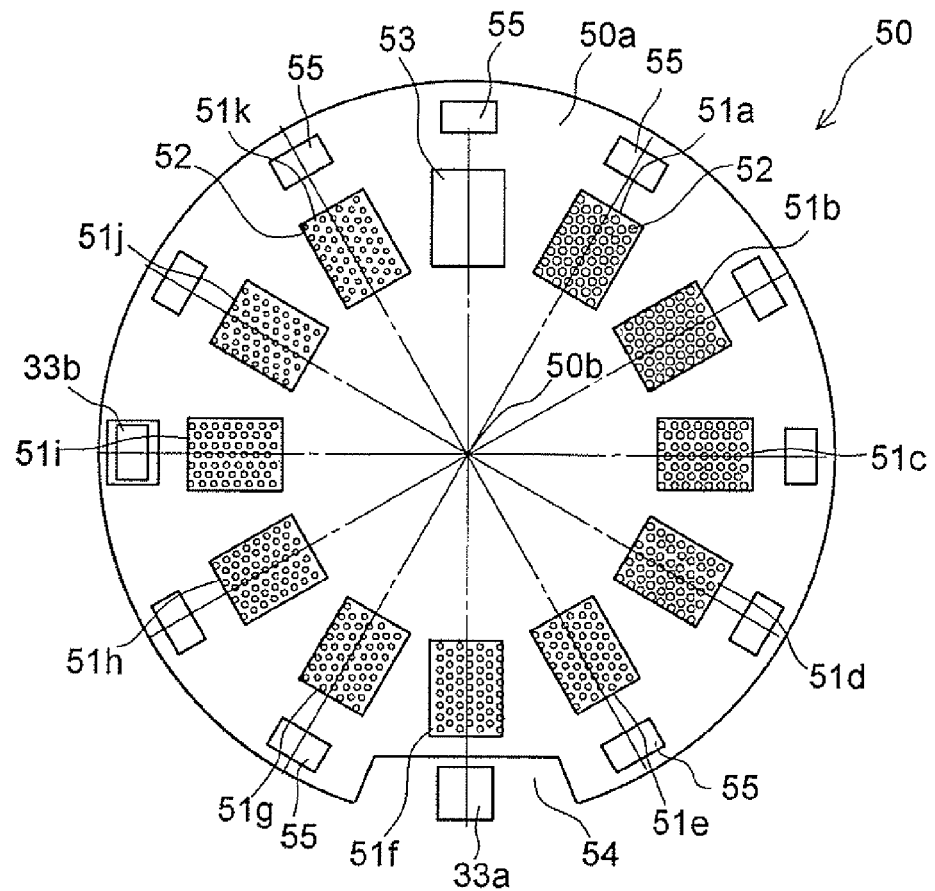
FIG. 6 is a front view of the rotary aperture plate of the aperture device of the light source unit, according to the present invention.

FIG. 6 is a front view of the rotary aperture plate 50 of the aperture device for the light source 23. As shown in FIG. 6, the rotary aperture plate 50 is made of an aluminum disc 50a. The disc 50a is fixed to a rotary shaft of the aperture plate drive motor 22 centered at the center of rotation 50b. The disc 50a has twelve openings which are formed at predetermined intervals circumferentially about the center of rotation 50b (at 30 degree intervals). In the illustrated embodiment, the disc 50a is provided with first to eleventh aperture openings 51a to 51k, and an auxiliary lamp opening 53. The first aperture opening 51*a* has an opening ratio of 70%. The opening ratios are determined to decrease stepwise, clockwise from the first aperture opening 51*a*. The second to eleventh aperture openings 51*b* to 51*k* have opening ratios of 50%, 35%, 25%, 18%, 13%, 9%, 7%, 5%, 3.5%, and 2%, respectively. The auxiliary lamp opening 53 has an opening ratio of 100%.

The rotary aperture plate 50 has a index detection hole (initial position detecting hole) 54 for detecting an initial position of rotation. An index sensor 33*a* is arranged so as to detect the index detection hole 54 when the rotary aperture plate 50 is in the initial position of rotation. An example of the index sensor 33*a* is a photo coupler. When the rotary aperture plate 50 is in the initial position, the index detection hole 54 opens the optical path of the index sensor 33*a* (photo coupler). In the illustrated embodiment, the index detection hole 54 of the rotary aperture plate 50 is formed open for 40 successive angular steps of rotation in the clockwise direction. The center of the third aperture opening 51*c* and the center of the illumination optical path (illumination optical axis O) coincide with each other after 20 successive angular steps of rotation from the position where the index detection hole 54 is first detected by the index sensor 33*a*.

Figure 7:
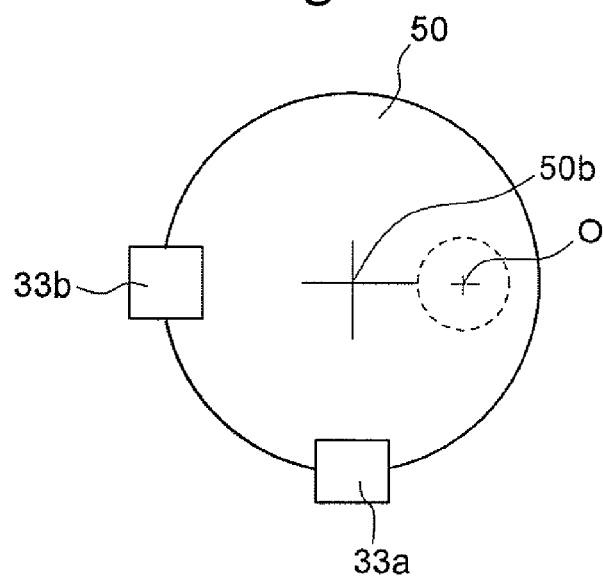
FIG. 7 is a diagram for explaining the physical relationship between the rotary aperture plate, an illumination optical axis, a index sensor, and an aperture position sensor, according to the present embodiment.

The rotary aperture plate 50 also has aperture position detection holes 55. The aperture position detection holes 55 are formed in predetermined positions in order to detect whether or not the centers of the aperture openings 51*a* to 51*k* and the auxiliary lamp opening 53 coincide with the illumination optical axis O, respectively. An aperture position sensor 33*b* (see FIGS. 6 and 7) which detects from the aperture position detection holes 55 whether or not the center of any one of the aperture openings 51*a* to 51*k* and the auxiliary lamp opening 53 coincides with the illumination optical axis O. The aperture position sensor 33*b* may also be a photo coupler likewise with the index sensor 33*a*.

The rotary aperture plate 50 may rotate slightly due to a sudden impact or the like. It is therefore desirable to form the aperture position detection holes 55 and the aperture position sensor 33*b* so as to successfully detect even a shift amount of, e.g., one to several steps in both directions (clockwise or anticlockwise directions).

In the illustrated embodiment, the index detection hole 54 and the aperture position detection holes 55 are formed at substantially the same distance from the center of rotation 50*b*. Therefore, the index detection hole 54 also serves as another aperture position detection hole 55. Since the index detection hole 54 is detected as one of the aperture position detection holes 55, the index detection hole 54 is elongated in the circumferential direction so as to continue being detected by the index sensor 33*a* for a plurality of steps (i.e., 40 steps in the illustrated embodiment). An elongated shape of the index detection hole 54 allows the index sensor 33*a* and the aperture position sensor 33*b* to distinguish the index detection hole 54 from the aperture position detection holes 55.

Figure 11:
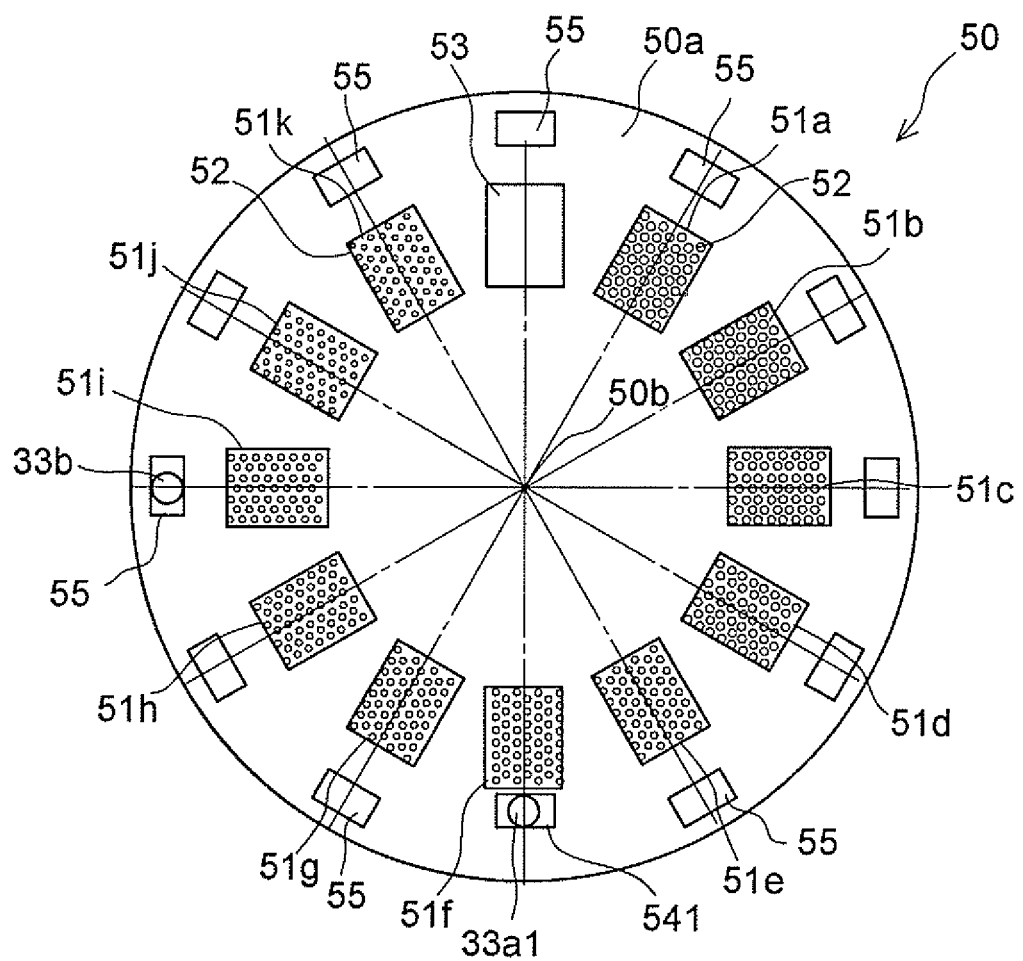
FIG. 11 is a front view of the rotary aperture plate of an alternative embodiment of the aperture device of the light source unit, according to the present invention.

Alternatively, it is possible for the index detection hole 54 and the aperture position detection holes 55 to be positioned at different distances from the center of rotation 50*b* so that the index detection hole 54 is not detected by the aperture position sensor 33 and the aperture position detection holes 55 are not detected by the index sensor 33*a*. For example, as shown in FIG. 11, an index detection hole 541 is formed as a position closer to the center of rotation 50*b*, and an index sensor 33*a*1 is provided at a position so as to detect the index detection hole 541. This construction makes it possible to distinguish the index detection hole 541 and the aperture position detection holes 55 without needing to elongate the index detection hole 541(54) in the circumferential direction or needing to rotate the rotary aperture plate 50 by a plurality of steps.

In the illustrated embodiment, the first to eleventh aperture openings 51*a* to 51*k* have a large number of small holes 52 which are formed at a predetermined spacing in each opening area (FIG. 6). The illumination light is either passed through these small holes 52 or blocked by the surface of the disc 50*a* where the small holes 52 are not formed.

In an embodiment, different opening ratios are achieved by modifying the density (spacing) of the small holes 52 of the first to eleventh aperture openings 51*a* to 51*k*. Alternatively, the density (spacing) can be maintained constant and the diameters of the small holes 52 can be modified. Alternatively, both the density (spacing) and the diameter of the small holes 52 can be modified. The small holes 52 can have any shape. Each of the first to eleventh aperture openings 51*a* to 51*k* may be provided with a mixture of small holes of various shapes, or may have small holes of respective different shapes. Although circular small holes are easy to form and to modify in diameter, polygonal and other shapes may also be adopted. Polygonal shapes can easily provide higher opening ratios than with circular shapes.

The rotary aperture plate 50 is driven stepwise by the aperture plate drive motor 22. It is desirable for the aperture plate drive motor 22 to be a stepping motor. In the illustrated embodiment, a stepping motor having a step angle of 0.75 degrees is used. Namely, when the aperture plate drive motor 22 rotates by 40 steps, the rotary aperture plate 50 is rotated by 30 degrees, i.e., by one aperture opening.

As shown in FIG. 5, the processor 10 has an auxiliary light 44 that comes into operation when the lamp 35 of the light source 23 goes out due to some reason. When the control circuit 41 detects that the lamp 35 goes out, the control circuit 41 activates an auxiliary light drive mechanism 45 to put the auxiliary light 44 into the illumination optical path and turn on the auxiliary light 44 ON. The control circuit 41 rotates the rotary aperture plate 50 so that the auxiliary lamp opening 53 enters (intersects) the illumination optical path.

Figure 8:
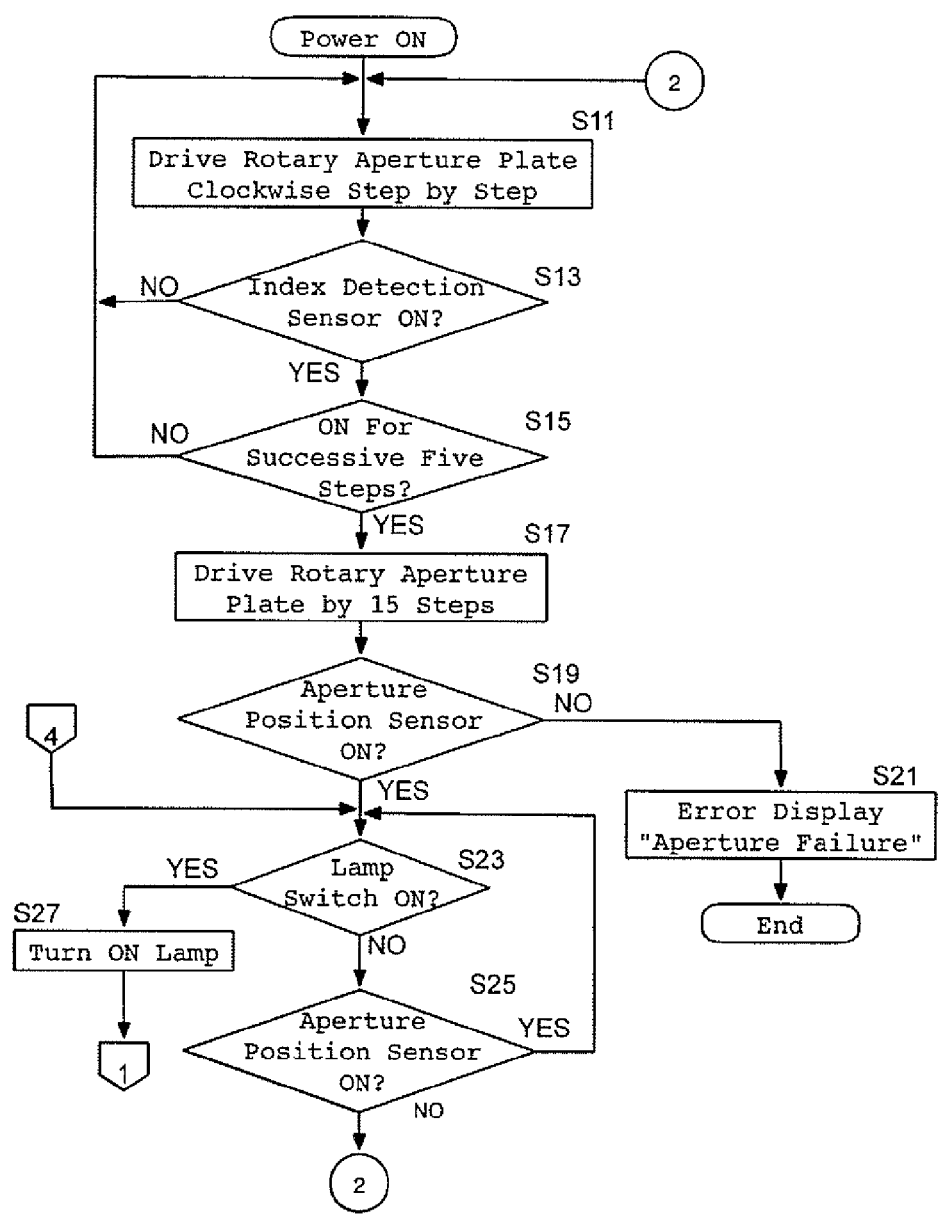
FIG. 8 is a flowchart showing a first half of a control operation pertaining to illumination of the processor.
Figure 9:
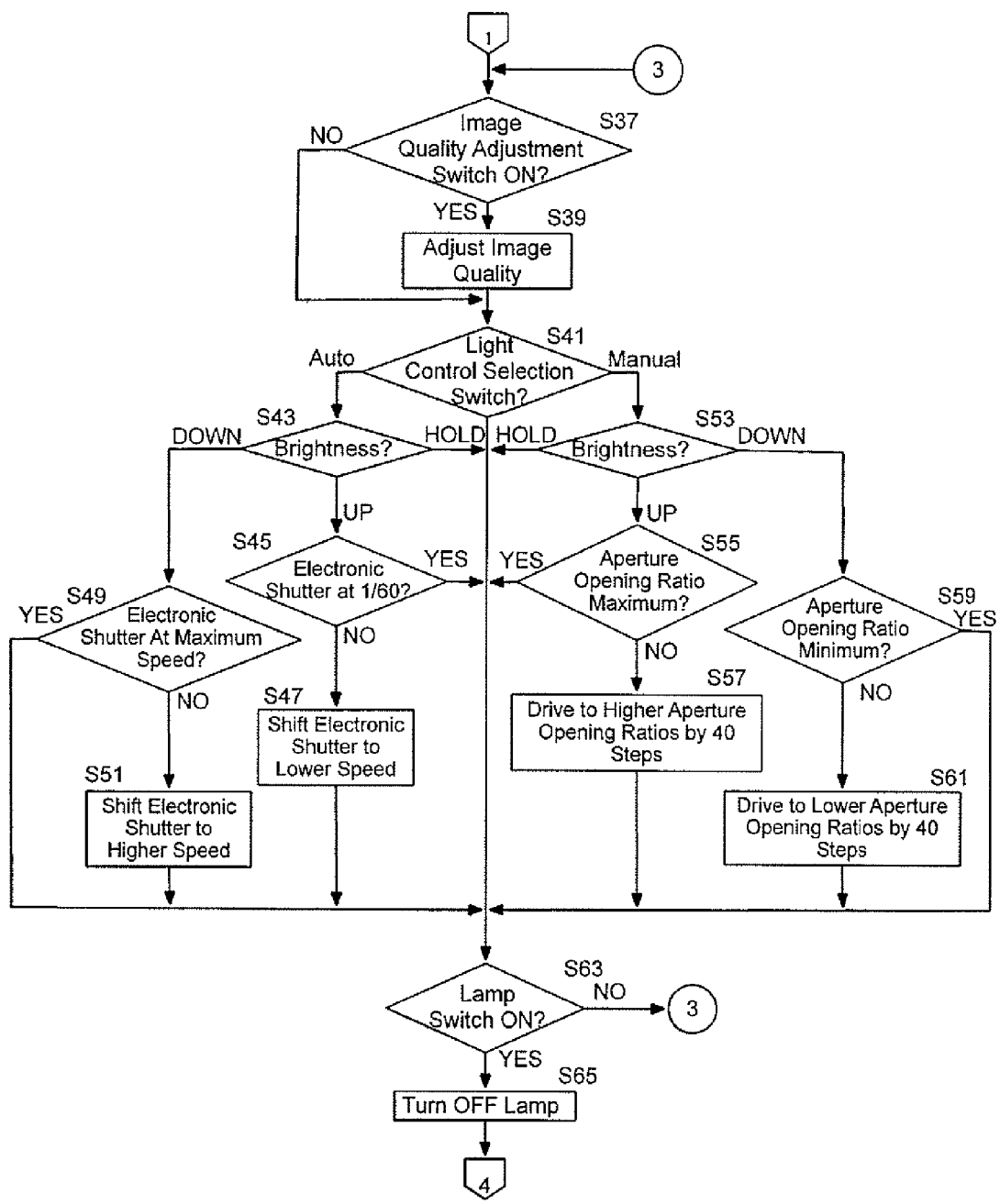
FIG. 9 is a flowchart showing a second half of the control operation pertaining to illumination of the processor.

The operation of the electronic endoscope system will be described with reference to the flowchart of the power-ON process shown in FIGS. 8 and 9. The power-ON process concerns the operation of the control circuit 41. The control circuit 41 enters this power-ON process when the main switch 15 is turned ON.

Upon entering the power-ON process, the control circuit 41 initially rotates the rotary aperture plate 50 stepwise in the clockwise direction (step S11). In the present embodiment, the aperture plate drive motor 22 is driven to rotate the rotary aperture plate 50 clockwise in units of one step.

Thereafter, the control circuit 41 checks whether or not the index sensor 33*a* is ON (step S13). If the index 33*a* is not ON (step S13, NO), control returns to step S11 to rotate the rotary aperture plate 50 clockwise by one step. If the index sensor 33*a* is ON (step S13, YES), the control circuit 41 checks whether or not the index sensor 33*a* stays ON for a first predetermined number of steps of rotation, i.e., five successive steps in the illustrated embodiment (step S15). If the index sensor 33*a* is not ON for five successive steps of rotation (step S15, NO), the control circuit 41 returns to step S11 to repeat the process of steps S11 through S15. If the index sensor 33*a* is ON for five successive steps of rotation (step S15, YES), the index sensor 33*a* has detected the index position hole 54.

If it is determined that the index sensor 33*a* has stayed ON for five successive steps (step S15, YES), the control circuit 41 further rotates the rotary aperture plate 50 clockwise by a second predetermined number of steps, i.e., fifteen steps (step S17). After the fifteen steps of rotation, the rotary aperture plate 50 reaches the initial position. According to the present embodiment, the initial position refers to the state where the aperture opening 51c, having an aperture opening ratio of 35%, is positioned in the illumination optical path.

Figure 10:
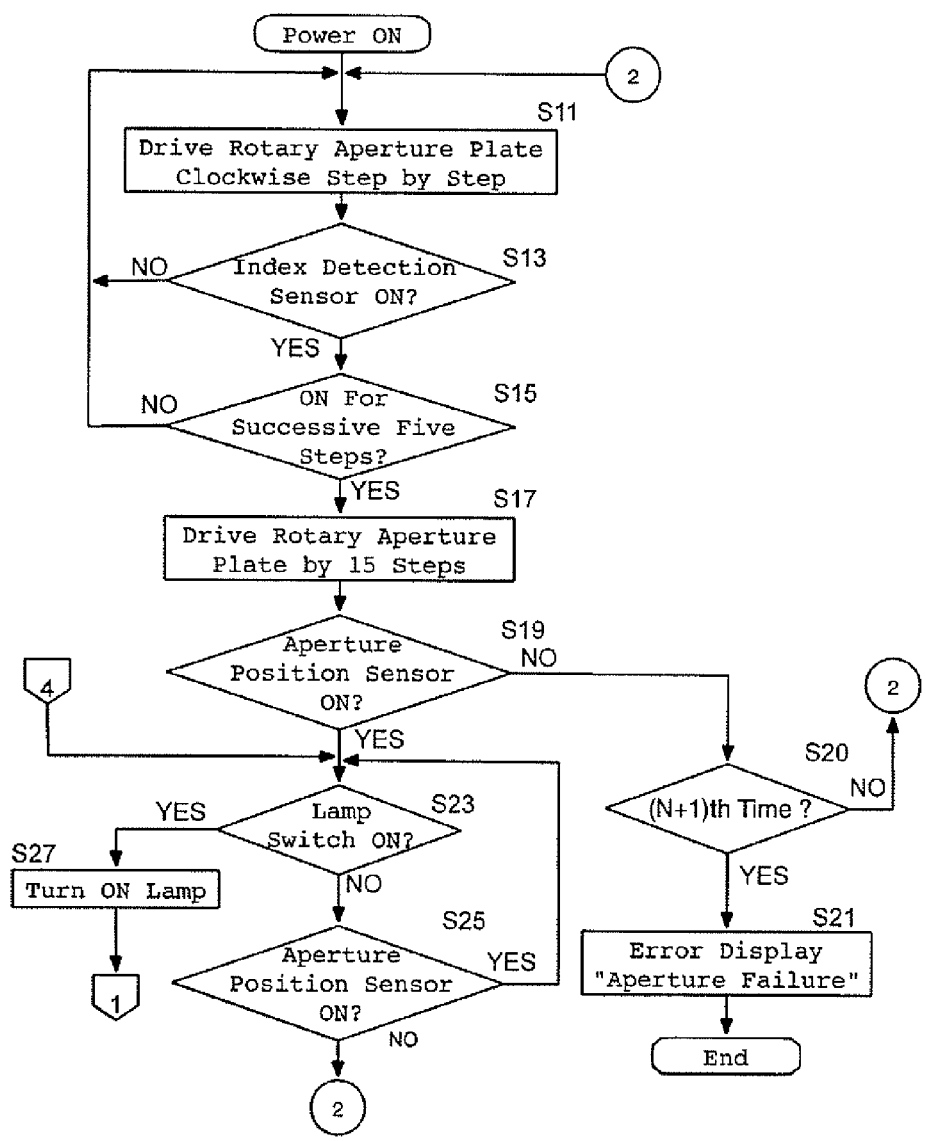
FIG. 10 is a flowchart showing a first half of a control operation pertaining to illumination of the processor, as an alternative embodiment to that shown in FIG. 8.

Thereafter, the control circuit 41 checks whether or not the aperture position sensor 33b is ON (step S19). If the aperture position sensor 33b is not ON (step S19, NO), the control circuit 41 displays an error indication, e.g., "APERTURE FAILURE," on the scope information display 20 or the monitor display 43 (step S21), and control ends. When the rotary aperture plate 50 is rotated by 20 steps after the edge of the index detection hole 54 is detected by the index sensor 33a, the aperture position sensor 33b detects (ON) an aperture position detection hole 55. Due to this construction, it is possible to determine that the rotary aperture plate 50 is out of position when the aperture position sensor 33b is not ON. In the illustrated embodiment, an error indication is issued and the power-ON process is ended if it is determined that the aperture position sensor 33b is not ON (step S19, NO). However, in an alternative embodiment, as shown in FIG. 10, it is possible to issue the error indication and end the power-ON process when the aperture position sensor 33b is not ON even after control is returned to step S11 and has repeated the initialization step a plurality of times (N times) (step S19, NO; S20, YES; S21; end).

If the aperture position sensor 33b is ON (step S19, YES), the control circuit 41 checks whether or not the lamp switch 16 is operated when the lamp 35 is OFF (step S23). If the lamp switch 16 is not operated (step S23, NO), the control circuit 41 checks whether or not the aperture position sensor 33b is ON (step S25). If the aperture position sensor 33b is ON (step S25, YES), the control circuit 41 returns to step S23. If the aperture position sensor 33b is not ON (step S25, NO), the control circuit 41 returns to step S11 because the rotary aperture plate 50 is determined as not being at a regular stop position. If the lamp switch 16 is operated (step S23, YES), the control circuit 41 turns ON the light source 23 (step S27), and proceeds to step S37. It should be noted that the lamp switch 16 in the illustrated embodiment is a momentary switch. The control circuit 41 turns ON the lamp 35 if the lamp switch 16 is operated when the lamp 35 is OFF, and turns OFF the lamp 35 if the lamp switch 16 is operated while the lamp 35 is ON.

As mentioned above, the indication of an aperture failure is issued when the aperture position sensor 33b fails to detect any of the aperture position detection holes 55 even after the index process (i.e., steps S11 through S17) is performed on the rotary aperture plate 50. The User can thus easily recognize that something is wrong with the rotary aperture plate 50.

In an alternative embodiment, if the index sensor 33a stays ON for five or more steps, the aperture plate drive motor 22 may be subsequently driven stepwise as long as the index sensor 33a is in the detecting state until the aperture position sensor 33b issues a detection signal. According to this construction, the possibility of the aperture position sensor 33b detecting an aperture position detection hole 55 increases even if the rotary aperture plate 50 rotates clockwise or counterclockwise due to an accidental impact, or the like, occurring during the index process.

At step S37 (see FIG. 9), the control circuit 41 checks whether or not the image quality adjustment switch 17 is ON. If the image quality adjustment switch 17 is ON, the control circuit 41 makes an image quality adjustment and proceeds to step S41 (step S37, YES; S39, S41). If the image adjustment switch 17 is not ON, the control circuit 41 skips the image quality adjustment and proceeds to step S41 (step S37, NO; S41).

At step S41, the control circuit 41 checks whether automatic light control or manual light control has selected by the light control selection switch 18.

If the automatic light control is selected (step S41, AUTO), the control circuit 41 checks whether to increase, decrease, or hold the brightness based on the brightness of the object image measured by the control circuit 41 (step S43). In order to increase the brightness (step S43, UP), i.e., adjust toward an overexposure, the control circuit 41 checks whether or not the electronic shutter is set to a minimum speed of 1/60 seconds (step S45). If the shutter speed is already set to 1/60 seconds, the control circuit 41 simply proceeds to step S63 since it is impossible to slow down the shutter speed further (step S45; YES, S63). If the shutter speed is not set to 1/60 seconds (step S45, NO), the control circuit 41 shifts the electronic shutter to a slower speed (step S47), and proceeds to step S63.

In order to decrease the brightness (step S43, DOWN), i.e., adjust toward an underexposure, the control circuit 41 checks whether or not the electronic shutter is set to a maximum speed (step S49). If the electronic shutter is set to the maximum speed (step S49. YES), the control circuit 41 simply proceeds to step S63. If the electronic shutter is not set to the maximum speed (step S49, NO), the control circuit 41 shifts the electronic shutter to a higher speed (step S51), and proceeds to step S63.

To hold the brightness (step S43; HOLD), i.e., make no adjustment on the exposure, the control circuit 41 simply proceeds to step S63.

If the manual light control is selected (step S41, MANUAL), the control circuit 41 checks whether brightness UP, DOWN, or HOLD has selected by the manual adjustment switch 19 (step S53). It should be noted that when the manual light control is selected in the illustrated embodiment, the electronic shutter speed is fixed to 1/60 seconds.

If brightness UP is selected by the manual adjustment switch 19 (step S53, UP), the control circuit 41 checks whether or not the aperture opening ratio is set to a maximum value. If the aperture opening ratio is set to the maximum value (step S55, YES), the control circuit 41 simply proceeds to step S63. If the aperture opening ratio is not set to the maximum value (step S55; NO), the control circuit 41 rotates the rotary aperture plate 50 to higher aperture opening ratios by 40 steps (step S57), and proceeds to step S63. In other words, the current aperture opening is switched to an adjacent aperture opening having a higher aperture opening ratio.

If brightness DOWN is selected by the manual adjustment switch 19 (step S53, DOWN), the control circuit 41 checks whether or not the aperture opening ratio is set to a minimum value (step S59). If the aperture opening ratio is set to the minimum value (step S59, YES), the control circuit 41 simply proceeds to step S63. If the aperture opening ratio is not set to the minimum value (step S59, NO), the control circuit 41 rotates the rotary aperture plate 50 to lower aperture opening ratios by 40 steps (step S61), and proceeds to step S63. In other words, the current aperture opening is switched to an adjacent aperture opening having a higher aperture opening.

If no selection is made by the manual adjustment switch 19 (step S53, HOLD), the control circuit 41 simply proceeds to step S63.

At step S63, the control circuit 41 checks whether or not the lamp switch 16 is operated while the lamp 35 is ON. If the lamp switch 16 is not operated (step S63, NO), control returns to step S37. If the lamp switch 16 is operated (step S63, YES), the control circuit 41 turns OFF the lamp 35 (S65) and control returns to step S23.

When the main switch 15 is turned OFF, the control circuit 41 turns OFF the lamp 23 and exits via an interrupt process.

It should be appreciated that the process of driving the rotary aperture plate 50 at steps S57 and S61 can include checking whether or not any of the aperture position detection holes 55 is detected by the aperture position sensor 33*b*. If none of the aperture position detection holes 55 are detected by the aperture position sensor 33*b*, the same index process as shown in steps S11 to S19 may be performed.

Obvious changes may be made in the specific embodiments of the present invention described herein, such modifications being within the spirit and scope of the invention claimed. It is indicated that all matter contained herein is illustrative and does not limit the scope of the present invention.

What is claimed is:

1. An endoscope light source unit for making illumination light from a light source incident on an incident end face of a light guide connected thereto, said endoscope light source unit comprising:
    an aperture device having a plurality of aperture openings of different opening ratios, for selectively positioning one of said aperture openings between said incident end face and said light source;
    a driving device for moving said aperture device;
    an index detection device for detecting whether a specific one of said aperture openings of said aperture device is positioned between said incident end face and said light source;
    an aperture opening position detection device for detecting whether any one of said aperture openings lies between the incident end face and the light source;
    a measuring device for measuring a driving amount of said driving device with respect to a position of said specific one of said aperture openings; and
    a controller for driving said driving device based on measurements from said index detection device, said aperture position detection device, and said measuring device.

2. The endoscope light source unit according to claim 1, wherein said aperture device comprises a rotary aperture disc;
    wherein said rotary aperture disc includes said aperture openings, a index detection hole for detecting whether said rotary aperture disc is at an initial position of rotation, and a plurality of aperture position detection holes for detecting whether any one of said aperture openings lies between said incident end face and said light source, said aperture openings being formed at regular intervals circumferentially about the center of rotation of said rotary aperture disc;
    wherein said index detection device includes an index sensor for detecting said index detection hole when the rotary aperture disc is at the initial position of rotation; and
    wherein said aperture opening position detection device includes an aperture position sensor for detecting whether any one of the aperture openings lies between said incident end face and said light source.

3. The endoscope light source unit according to claim 2, wherein said driving device comprises a stepping motor for driving said rotary aperture disc to rotate step by step in units of a predetermined angle;
    wherein said measuring device measures a number of steps by which said stepping motor is driven from said initial position of rotation; and
    wherein said index detection hole is formed so as to be continually detected by said index sensor while the stepping motor is driven to rotate by a first predetermined number of steps in one direction, and further driven by a second predetermined number of steps in the same direction, and wherein one of said aperture position detection holes is detected by said aperture position sensor when driven by said second predetermined number of steps.

4. The endoscope light source unit according to claim 3, wherein said controller drives the stepping motor step by step until the index censor detects said index detection hole in the case where none of said aperture position detection holes are detected by said aperture position sensor after said first and second predetermined numbers of steps of driving.

5. The endoscope light source unit according to claim 4, wherein said index detection hole and said aperture position detection holes are formed at substantially same distances from the center of rotation of said rotary aperture disc; and
    wherein said index detection hole is formed elongated in a circumferential direction of said rotary aperture disc so that said index detection hole continues to be detected by said index sensor while said stepping motor is rotated by a plurality of steps.

6. The endoscope light source unit according to claim 4, wherein said index detection hole and said aperture position detection holes are formed at different distances from the center of rotation of said rotary aperture disc so that said index detection hole is detected only by said index sensor and said aperture position detection holes is detected by said aperture position sensor.

7. The endoscope light source unit according to claim 3, further comprising a display device for displaying an error indication when none of said aperture position detection holes is detected by said aperture position sensor after said first and second predetermined numbers of steps of driving.

* * * * *